(12) United States Patent
Brinsfield et al.

(10) Patent No.: US 6,556,630 B1
(45) Date of Patent: Apr. 29, 2003

(54) DUAL BAND TELEMETRY SYSTEM

(75) Inventors: James W. Brinsfield, Mequon, WI (US); Michael F. Steinike, Grafton, WI (US); Jeffrey S. Wells, Jackson, WI (US)

(73) Assignee: GE Medical Systems Information Technologies, Waukesha WI ( * ) Notice: Subject to any disclaimer, the term of this patent is extended or adjusted under 35 U.S.C. 154(b) by 0 days.

(21) Appl. No.: 09/474,593

(22) Filed: Dec. 29, 1999

(51) Int. Cl.$^7$ ............................................... H04L 27/16
(52) U.S. Cl. ............... 375/335; 340/870.11; 455/188.1; 455/180.1; 375/349
(58) Field of Search ....................... 340/870.28, 870.02, 340/870.11; 455/120, 121, 188, 188.1, 188.2, 189.1, 191.1; 375/324, 335, 340, 316, 349, 211, 214

(56) References Cited

U.S. PATENT DOCUMENTS

| | | | |
|---|---|---|---|
| 3,639,907 A | 2/1972 | Greatbatch | |
| 4,658,831 A | 4/1987 | Reinhard et al. | |
| 4,675,656 A | 6/1987 | Narcisse | |
| 4,689,627 A | 8/1987 | Lee et al. | |
| 4,827,943 A | 5/1989 | Bornn et al. | |
| 4,958,645 A | * 9/1990 | Cadell et al. ................ | 600/484 |
| 5,093,922 A | * 3/1992 | Kubo et al. .................. | 455/315 |
| 5,153,584 A | 10/1992 | Engira | |
| 5,205,294 A | 4/1993 | Flach et al. | |
| 5,319,363 A | 6/1994 | Welch et al. | |
| 5,396,224 A | 3/1995 | Dukes et al. | |
| 5,458,123 A | 10/1995 | Unger | |
| 5,579,001 A | 11/1996 | Dempsey et al. | |
| 5,579,775 A | 12/1996 | Dempsey et al. | |
| 5,687,734 A | 11/1997 | Dempsey et al. | |
| 5,694,940 A | 12/1997 | Unger et al. | |
| 5,745,523 A | * 4/1998 | Dent et al. ................... | 375/216 |
| 5,855,550 A | 1/1999 | Lai et al. | |
| 6,041,222 A | * 3/2000 | Horton et al. ........... | 455/188.1 |
| 6,115,584 A | * 9/2000 | Tait et al. .................... | 455/120 |
| 6,144,846 A | * 11/2000 | Durec ......................... | 327/113 |
| 6,151,488 A | * 11/2000 | Brekelmans ............. | 455/150.1 |
| 6,195,563 B1 | * 2/2001 | Samuels ..................... | 455/553 |
| 6,208,875 B1 | * 3/2001 | Damgaard et al. .......... | 455/260 |
| 6,359,940 B1 | * 3/2002 | Ciccarelli et al. ........... | 375/316 |

\* cited by examiner

Primary Examiner—Michael Horabik
Assistant Examiner—Hung Dang
(74) Attorney, Agent, or Firm—Michael Best & Friedrich, LLP

(57) ABSTRACT

A dual band telemetry system useful for monitoring patients in a care unit of a health care facility. The system includes an antenna system with a first antenna tuned to receive a signal in a first frequency band, a second antenna tuned to receive a signal in a second frequency band, a down converter for producing a frequency translation signal, and a mixer coupled to the second antenna. The mixer combines the signal received by the second antenna with the frequency translation signal to produce a signal having a frequency in the first frequency band. A combiner coupled to the mixer and the first antenna combines the signal generated by the mixer with the signal received by the first antenna. The combined signals are ultimately delivered to a central station for processing.

30 Claims, 3 Drawing Sheets

DUAL BAND TELEMETRY SYSTEM

BACKGROUND OF THE INVENTION

The present invention relates to systems and devices for monitoring patients in a healthcare facility and particularly to patient monitoring systems that allow the patient to ambulate through a care unit in the facility.

Most patient monitoring systems that permit patients to ambulate through a care unit use telemetry-based communication schemes. In one common form, the patient wears a telemetry transmitter attached to the patient using ECG electrodes. The telemetry transmitter acquires an ECG signal, conducts a nominal amount of filtering on the ECG signal, and transmits a telemetry data signal to an antenna array, typically located in the ceiling of the care unit. The telemetry signal is conducted through the antenna array to a telemetry receiver, which in turn, is connected to a central station that analyzes and displays the ECG information for viewing and evaluation by the clinicians staffing the care units.

Existing medical telemetry systems are regulated by the Federal Communications Commission ("FCC") and are required to use VHF (very high frequency) and UHF (ultra high frequency) radio-frequency ("RF") bands for their wireless data links. Presently, it is necessary to install two separate telemetry infrastructures or systems to utilize both of these bands. Of course, installing two systems increases the cost of patient monitoring. Proposed changes in FCC regulations will provide a new band (the L-band) in the RF spectrum for medical telemetry systems. While the addition of the new band will provide new capacity for telemetry systems and help reduce interference with other RF signals, operating in the new band with current technology would require an additional and separate telemetry infrastructure. However, if L-band telemetry systems could be implemented without additional infrastructure, significant cost savings could be realized.

SUMMARY OF THE INVENTION

Accordingly, the present invention provides a dual band telemetry system that is capable of receiving both UHF and L-band signals. The architecture of the system permits the detection and processing of L-band and UHF signals with a common receiver and antenna system, thereby eliminating costly, redundant infrastructure that would otherwise be required.

The system includes an antenna system having a first antenna tuned to receive a signal having a frequency in a first frequency band, a second antenna tuned to receive a signal having a frequency in a second frequency band, a down converter for producing a frequency translation signal, and a mixer coupled to the second antenna and the down converter. The mixer combines the signal received by the second antenna with the frequency translation signal to produce a signal having a frequency in the first frequency band. In other words, the mixer converts the signal received by the second antenna to a signal in the first frequency band. A combiner coupled to the mixer and the first antenna combines the signal generated by the mixer with the signal received by the first antenna. The combined signals are then delivered to a receiver station or subsystem designed to receive signals in the first frequency band.

One advantage of the present invention is that it eliminates the need to provide a receiver subsystem capable of processing signals in the second frequency band. The signal received by the second antenna is converted to a signal in the first frequency band and, thus, may be processed by the same receiver subsystem that processes signals from the first antenna.

Preferably, the dual band telemetry system of the present invention is designed to operate with RF signals. In particular, the first antenna is designed to receive UHF signals and the second antenna is designed to receive L-band signals. The first antenna is designed to receive signals in a particular channel within the UHF band and the signals from the second antenna are converted to a second channel in the UHF band before detection at the receiver station.

The down converter is designed so that the frequency of the translation signal may be selected so that the converted signal produced by the mixer falls within the second channel in the first frequency. The frequency of the second channel depends on factors such as avoiding interference with other RF signals including the signal from the first antenna and local UHF signals from television broadcasts. To set an appropriate frequency for the translation signal, the down converter uses an oscillator, a synthesizer, and a filter coupled in a series loop (i.e., the components form a phase-lock loop). The synthesizer is programmed through a microprocessor that can receive input from a technician, administrator, or similar person to adjust the frequency. The synthesizer derives its frequency reference from a temperature controlled oscillator to compensate for temperature changes.

The antenna system is designed to work with telemetry transmitters worn by patients in a care unit, a receiver subsystem, and a central station. The transmitters acquire patient data and transmit that data at a predetermined frequency. In its simplest form, the system operates with one telemetry transmitter that operates in the first frequency band and a second transmitter that operates in the second frequency band. The signals sent by the telemetry transmitters are received by the first and second antennas and the signal from the second antenna is converted as described above. The signal from the first antenna and the converted signal are then relayed to the receiver subsystem which in turn delivers the signals to a central station. The patient data is collected and analyzed at the central station.

As is apparent from the above, it is an advantage of the present invention to provide a multiple band telemetry system that requires only one receiver subsystem and central station. Other features and advantages of the present invention will become apparent by consideration of the detailed description and accompanying drawings.

DETAILED DESCRIPTION

Figure 1:
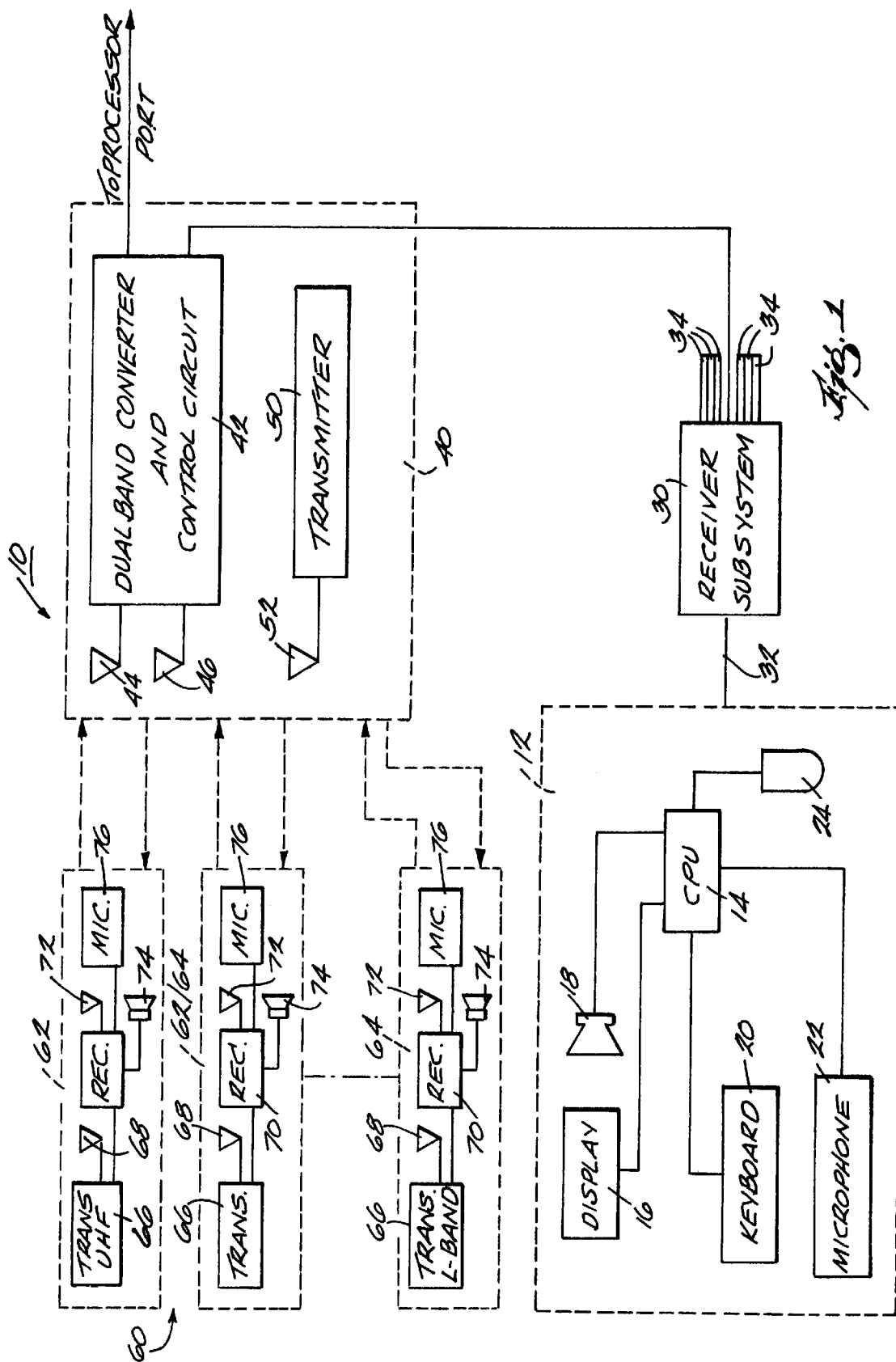
FIG. 1 is a block diagram of a dual band telemetry system embodying the invention.

Before one embodiment of the invention is explained in detail, it is to be understood that the invention is not limited in its application to the details of the construction and the arrangements of the components set forth in the following description or illustrated in the drawings. The invention is capable of other embodiments and of being practiced or being carried out in various ways. Also, it is to be understood that the phraseology and terminology used herein is for the purpose of description and should not be regarded as limiting.

FIG. 1 illustrates a dual band telemetry system 10 embodying the invention. As is commonly known in the art, the system 10 includes a central station 12. The central station 12 includes a processing unit or processor 14, which, in its most common form is a computer. The processor 14 is coupled to a display 16 and speaker 18 and may receive input from a keyboard 20, a microphone 22, or a mouse 24. The central station 12 is connected to a receiver subsystem 30 through a communication link 32. The receiver subsystem 30 includes a series of I/O ports 34 connected to a plurality of antennas 40 (only one of which is shown) spaced about the care unit to form an antenna array. While the number of antennas 40 may vary in any particular application, typically, each antenna 40 is identical.

The antenna 40 includes a converter and control circuit 42. The converter and control circuit 42 is coupled to a first RF antenna 44 tuned to receive signals having a frequency within a first frequency band and a second antenna 46 tuned to receive signals having a frequency in a second frequency band. The antenna unit 40 also includes an antenna transmitter circuit 50 connected to a transmitter antenna 52. The antenna transmitter 50 generates an RF signal which may be used to transmit commands and information from the central station 12 to the telemetry transmitters discussed below.

The dual band telemetry system 10 includes a plurality of telemetry transmitters 60. The telemetry transmitters 60 may be one of two types. A first type 62 is designed to operate in a first frequency band (such as UHF) and a second type 64 is designed to operate in a second frequency band (such as L-band). As is known to those of ordinary skill in the art, the UHF telemetry band generally covers frequencies of about 470 MHz to about 668 MHz. The L-band generally covers signals having frequencies of about 1 GHz to about 2 GHz and, more particularly, about 1.4 GHz.

In use, each telemetry transmitter 60 is connected to a patient (not shown) via electrodes or connections suitable for measuring patient parameters (such as ECG electrodes). Once a telemetry transmitter 60 is connected to a patient, the patient's condition may be monitored. Due to the wireless nature of the telemetry transmitters, the patient's ability to ambulate throughout the care unit is unhindered by the transmitter. Each telemetry transmitter 60 (regardless of type) includes a transmitter circuit 66 connected to a transmitting antenna 68. The transmitter circuit 68 generates an RF carrier signal for transmitting patient and other data to the antenna unit 40. As noted previously, the frequency of the carrier signal is dependent on the type of telemetry transmitter used: type 62 (UHF) or type 64 (L-band).

Each telemetry transmitter also includes a receiver circuit 70 connected to a receiving antenna 72, a speaker 74, and a microphone 76. The receiver circuit 70 includes support circuitry, power inputs, and common connections, as those of ordinary skill in the art would understand. The receiver circuit 70 also has a microprocessor input (not shown) connected to a microprocessor (not shown) of the telemetry transmitter. The microprocessor receives all physiological data and routes that data to the transmitter circuit 66. The microprocessor also processes the commands received by the receiver circuit 70 from the transmitter circuit 50 of the antenna 40.

Figure 2:
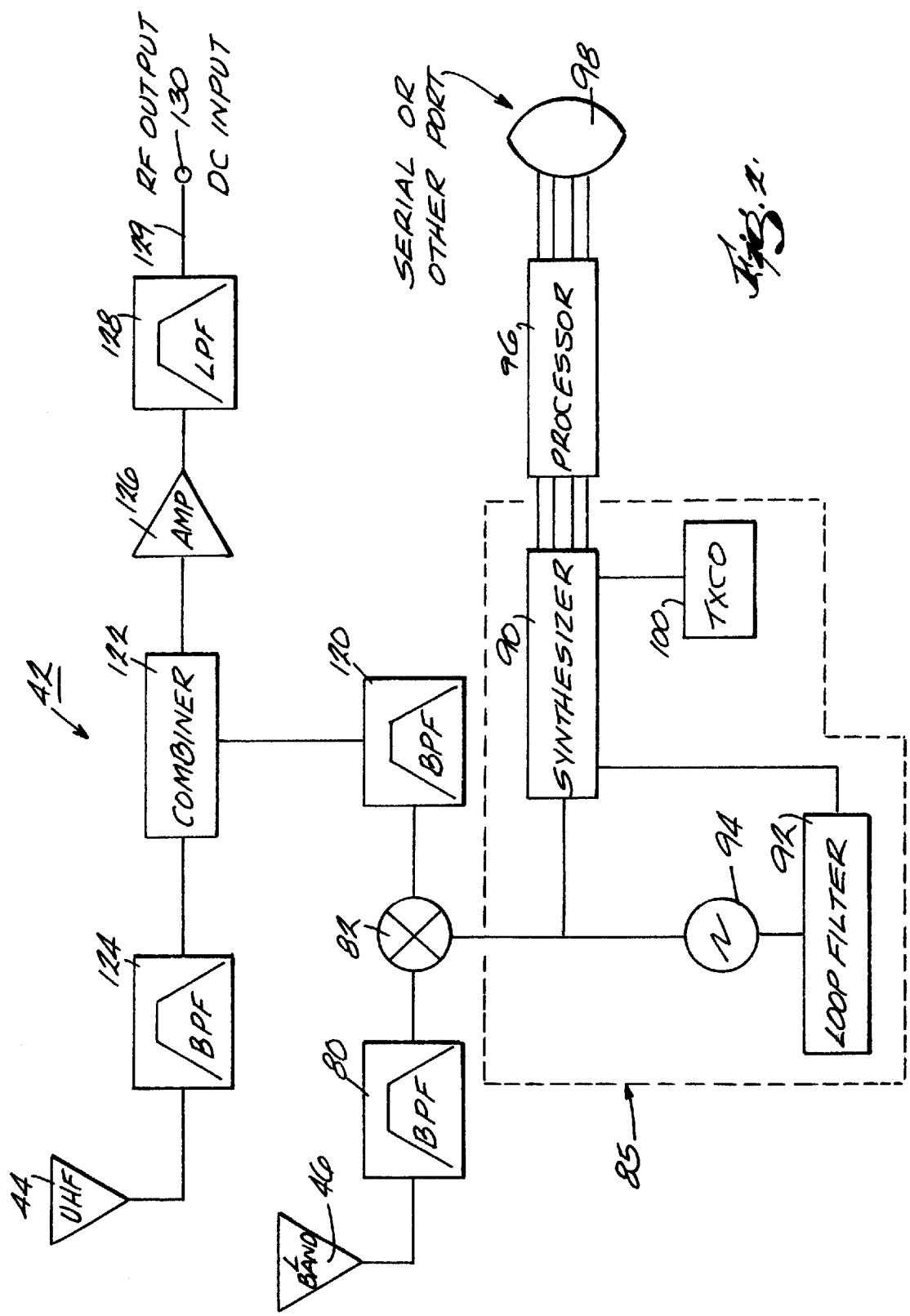
FIG. 2 is a block diagram of a converter and control unit that may be used in the telemetry system of FIG. 1.

One important feature of the system 10 is the converter and control circuit 42 of the antenna 40. As best seen by reference to FIG. 2, the converter and control circuit 42 is designed such that both L-band and UHF signals may be processed by the receiver substation 30 and central station 12. The control circuit 42 receives signals from the UHF antenna 44. UHF antenna 44 receives signals from the UHF telemetry transmitter 62 in an available UHF channel. By way of example, one UHF channel is channel 37 and this channel resides in the 6 MHz frequency band from 608 MHz to 614 MHz.

The control circuit 42 also receives signals from L-band antenna 46. L-band antenna 46 receives signals from the L-band telemetry transmitter 64 in an available L-band channel. The signal from the L-band antenna 46 is filtered by an L-band band pass filter 80 which removes signals outside of the L-band frequency range. The band-pass filter 80 also attenuates signals from a voltage-controlled oscillator (discussed below) to minimize emission of the voltage-controlled oscillator at the antenna 46. The L-band signals are delivered to a mixer 82, such as a JMS-5 mixer from Mini Circuits. The mixer 82 mixes the L-band signal with a frequency translation signal from a local oscillator 85 to produce a UHF band signal. The frequency translation signal is formed such that the UHF band signal generated by the mixer 82 resides in a different channel than the UHF signal received by the UHF antenna 44. Thus, in the case where the UHF antenna operates in channel 37, the signal generated by the mixer 82 would reside in a different channel, for example, channel 40.

Figure 3:
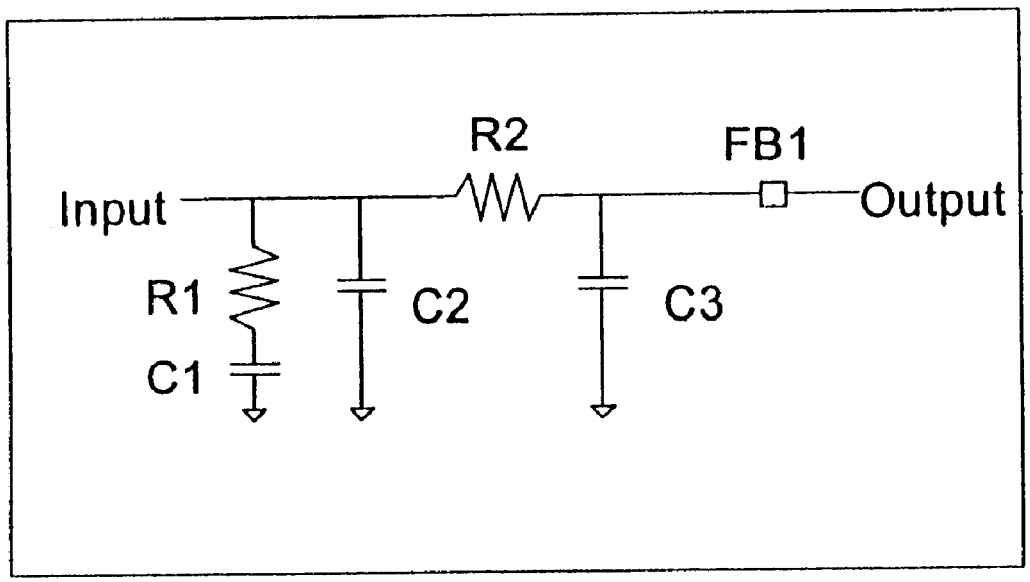
FIG. 3 is a circuit diagram of a filter suitable for use in a synthesizer local oscillator of the present invention.

The local oscillator 85 includes a synthesizer 90, such as the LMX2316 from National Semiconductor. The synthesizer is coupled in a series loop with a loop filter 92 and a voltage controlled oscillator 94. A loop filter suitable for use in the present invention is shown in FIG. 3. The voltage-controlled oscillator 94 may be one of several oscillators commercially available including those from Vari-L Company.

The synthesizer 90 is programmed by a microprocessor 96, which may be a commercially available processor such as a Microchip PIC16C620. The microprocessor 96 receives input through a port 98 such as a serial port. Information and commands delivered through the serial port 98 permit adjustment of the synthesizer frequency. The synthesizer 90 also receives input from a temperature controlled oscillator 100. The oscillator 100 provides the frequency reference for the synthesizer 90. The temperature controlled oscillator 100 may be implemented with commercially available oscillators such as an Oscillatek OSC-1B2 TCXO.

The output of the synthesizer 90 is delivered to the loop filter 92 which attenuates any reference spurs generated by the synthesizer 90, filters the noise in the loop, and controls the stability of the phase-lock loop. The voltage-controlled oscillator 94 oscillates at a frequency appropriate to achieve the desired translation frequency of the L-band signal so that it is down converted. The oscillation frequency of the voltage controlled oscillator 94 is set by the DC voltage received from the loop filter 92. The voltage-controlled oscillator produces a frequency translation signal that is delivered to the mixer 82. The frequency translation signal and the L-band signal from the antenna 46 are mixed in the mixer 82 and the resulting UHF signal is delivered to a band pass filter 120 which removes signals outside of the UHF frequency band. The filtered UHF signal is then delivered to a combiner 122, which may be a commercially available combiner such as a Mini Circuits JPS-2-900.

The combiner 122 also receives the UHF signal from the UHF antenna 44 as filtered by a band pass filter 124, which removes signals outside of the channel to which the antenna 44 is tuned. The combiner combines the UHF signals from the antenna 44 and mixer 82 and delivers them to an amplifier 126. After being amplified, the combined signals are filtered by a low pass filter 128, which removes harmonics of the two signals. The combined signals are output along a transmission line 129 to RF output node 130 (which also may serve as a DC input node) and are delivered to the receiver subsystem as described above.

As can be seen from the above, the present invention provides a dual band telemetry system for collecting information from telemetry transmitters worn by patients.

Various features and advantages of the invention are set forth in the following claims.

What is claimed is:

1. A dual band telemetry system comprising:
   a first antenna tuned to receive a signal having a frequency in a first RF band;
   a second antenna tuned to receive a signal having a frequency in a second RF band;
   a down converter for producing a frequency translation signal;
   a mixer coupled to the second antenna and to the down converter such that the mixer uses the signal received by the second antenna and the frequency translation signal to produce a signal having a frequency in the first RF band; and
   a combiner for combining the signal having a frequency in the first RF band with the signal received by the first antenna.

2. A dual band telemetry system as set forth in claim 1, wherein the first RF band is the UHF band and the second RF band is the L-band.

3. A dual band telemetry system as set forth in claim 1, wherein the down converter further comprises:
   an oscillator;
   a synthesizer; and
   a filter, the oscillator, the synthesizer, and the filter coupled in a series loop, the synthesizer coupled to a temperature controlled oscillator and a processor having an input.

4. A dual band telemetry system set forth in claim 1, further comprising:
   a first band pass filter coupled between the first antenna and the combiner and for blocking signals having frequencies outside a predetermined channel in the first RF band;
   a second band pass filter coupled between the second antenna and the mixer and for blocking signals having frequencies outside the second RF band; and
   a third band pass filter coupled between the mixer and the combiner and for blocking signals outside the first RF band.

5. A dual band telemetry system as set forth in claim 4, further comprising:
   a transmission line coupled to the combiner and for carrying signals in the first RF band.

6. A dual band telemetry system as set forth in claim 4, further comprising:
   an amplifier coupled to the combiner; and
   a low-pass filter coupled to the amplifier.

7. A dual band telemetry system comprising:
   a first telemetry transmitter for acquiring patient data and transmitting the patient data in a first signal having a frequency in a first RF band;
   a second telemetry transmitter for acquiring patient data and transmitting the patient data in a second signal having a frequency in a second RF band;
   an antenna array for receiving the first and second signals from the first and second telemetry transmitters, the antenna array including
      a first antenna tuned to receive a signal having a frequency in the first RF band,
      a second antenna tuned to receive a signal having a frequency in the second RF band,
      a down converter for producing a frequency translation signal,
      a mixer coupled to the second antenna and to the down converter, the mixer for using the signal received by the second antenna and the frequency translation signal to produce a signal having a frequency in the first RF band; and
      a combiner for combining the signal having a frequency in the first RF band with the signal received by the first antenna;
   a receiver subsystem coupled to the combiner; and
   a central station coupled to the receiver subsystem and for receiving the patient data.

8. A dual band telemetry system as set forth in claim 7, wherein the first RF band is the UHF band and the second RF band is the L-band.

9. A dual band telemetry system as set forth in claim 7, wherein the down converter further comprises:
   an oscillator;
   a synthesizer; and
   a filter, the oscillator, the synthesizer, and the filter coupled in a series loop, the synthesizer coupled to a temperature controlled oscillator and a processor having an input.

10. A dual band telemetry system set forth in claim 7, further comprising:
    a first band pass filter coupled between the first antenna and the combiner and for blocking signals having frequencies outside a predetermined channel in the first RF band;
    a second band pass filter coupled between the second antenna and the mixer and for blocking signals having frequencies outside the second RF band; and
    a third band pass filter coupled between the mixer and the combiner and for blocking signals outside the first RF band.

11. A dual band telemetry system as set forth in claim 10, further comprising
    a transmission line coupled to the combiner and for carrying signals in the first RF band.

12. A dual band telemetry system as set forth in claim 10, further comprising
    an amplifier coupled to the combiner; and
    a low-pass filter coupled to the amplifier.

13. A dual band telemetry system comprising:
    a first antenna tuned to receive a signal having a frequency in a first frequency band;
    a combiner coupled to the first antenna;
    a second antenna tuned to receive a signal having a frequency in a second frequency band;
    a mixer coupled to the second antenna and the combiner; and
    an oscillator coupled to the mixer and having an output, and wherein the mixer is configured to mix signals received from the second antenna with the output of the oscillator to produce a signal within the first frequency band.

14. A dual band telemetry system as set forth in claim 13, wherein the first antenna is tuned to receive a signal in a first channel within the first frequency band, the second antenna is tuned to receive a signal in a first channel within the second frequency band, and the mixer is operable to produce a signal in a second channel within the first frequency band.

15. A dual band telemetry system as set forth in claim 14, wherein the first frequency band is the UHF band and the second frequency band is the L-band.

16. A dual band telemetry system as set forth in claim 15, further comprising
a transmission line coupled to the combiner and for carrying signals in the first and second channels and an input power signal.

17. A dual band telemetry system as set forth in claim 13, further comprising:
a first telemetry transmitter for acquiring patient data and transmitting the patient data in a first signal having a frequency in the first frequency band;
a second telemetry transmitter for acquiring patient data and transmitting the patient data in a second signal having a frequency in the second frequency band;
a receiver subsystem coupled to the combiner; and
a central station coupled to the receiver subsystem and for receiving the patient data,
wherein the first antenna is tuned to receive the first signal from the first transmitter and the second antenna is tuned to receive the second signal from the second transmitter.

18. A dual band telemetry system as set forth in claim 17, further comprising:
a synthesizer; and
a filter, such that the oscillator, the synthesizer, and the filter are coupled in a series loop.

19. A dual band telemetry system as set forth in claim 18, further comprising:
a processor coupled to the synthesizer and having an input; and
a temperature controlled oscillator coupled to the synthesizer.

20. A dual band telemetry system as set forth in claim 14, further comprising:
a first band pass filter coupled between the first antenna and the combiner and for blocking signals having frequencies outside the first channel in the first frequency band;
a second band pass filter coupled between the second antenna and the mixer and for blocking signal having frequencies outside the first channel in the second frequency band; and
a third band pass filter coupled between the mixer and the combiner and for blocking signals outside of the first frequency band.

21. A dual band telemetry system as set forth in claim 20, further comprising
an amplifier coupled to the combiner; and
a low-pass filter coupled to the amplifier.

22. A method of monitoring patients in a care unit, the method comprising:
acquiring a patient data signal from a first transmitter that operates in a first frequency band;
acquiring a patient data signal from a second transmitter that operates in a second frequency band;
converting the patient data signal from the second transmitter to a third signal in the first frequency band;
combining the first and third signals; and
delivering the combined first and third signals to a receiver.

23. A method as set forth in claim 22, wherein the first frequency band is the UHF band and the second frequency band is the L-band.

24. A method as set forth in claim 22, wherein the act of acquiring a patient data signal from a first transmitter is accomplished using a first antenna tuned to receive a signal in a first channel within the first frequency band, and the act of acquiring a patient data signal from a second transmitter is accomplished using a second antenna tuned to receive a signal in a first channel within the second frequency band.

25. A method as set forth in claim 22, wherein the act of converting the patient data signal from the second transmitter to a third signal includes mixing the patient data signal from the second transmitter with a frequency translation signal from a local oscillator.

26. A method as set forth in claim 22, further comprising filtering the combined first and third signals prior to delivering the combined first and third signals to a receiver.

27. A method as set forth in claim 22, further comprising filtering the patient data signal from a first transmitter to remove frequencies outside a first channel in the first frequency band.

28. A method as set forth in claim 22, further comprising filtering the patient data signal from a second transmitter to remove frequencies outside a first channel in the second frequency band.

29. A method as set forth in claim 22, further comprising filtering the third signal to remove frequencies outside of the first frequency band.

30. A method as set forth in claim 22, further comprising processing the first and third signals at a central station.

* * * * *